United States Patent [19]

Sato et al.

[11] Patent Number: 4,464,229
[45] Date of Patent: Aug. 7, 1984

[54] PROCESS FOR PRODUCING ACRYLIC OR METHACRYLIC ESTERS

[75] Inventors: Takahisa Sato; Sumio Nakashima; Masao Baba, all of Himeji, Japan

[73] Assignee: Nippon Shokubai Kagaku Kogyo Co. Ltd., Osaka, Japan

[21] Appl. No.: 393,484

[22] Filed: Jun. 29, 1982

[30] Foreign Application Priority Data

Jul. 9, 1981 [JP] Japan ................. 56-106228
Jul. 29, 1981 [JP] Japan ................. 56-117786
Nov. 2, 1981 [JP] Japan ................. 56-174557

[51] Int. Cl.$^3$ ............... B01D 3/26; B01D 3/34; C07C 67/035; C07C 67/54
[52] U.S. Cl. ............... 203/60; 203/DIG. 21; 560/218
[58] Field of Search .......... 203/60, DIG. 6, DIG. 16, 203/DIG. 21, DIG. 25; 560/218

[56] References Cited

U.S. PATENT DOCUMENTS

| | | | |
|---|---|---|---|
| 3,743,672 | 7/1973 | Kollar | 203/DIG. 6 |
| 3,882,167 | 5/1975 | Lohmar et al. | 203/DIG. 6 |
| 3,914,290 | 10/1975 | Otsuki et al. | 203/DIG. 21 |
| 3,951,756 | 4/1976 | Dirks et al. | 203/DIG. 21 |
| 4,076,950 | 2/1978 | Stewart et al. | 560/218 |
| 4,250,328 | 2/1981 | Fujita et al. | 203/DIG. 6 |

FOREIGN PATENT DOCUMENTS

| | | | |
|---|---|---|---|
| 2832202 | 2/1979 | Fed. Rep. of Germany | 203/DIG. 21 |
| 54-122210 | 9/1979 | Japan | 203/DIG. 21 |
| 55-105645 | 8/1980 | Japan | 203/DIG. 6 |

*Primary Examiner*—Bradley Garris
*Attorney, Agent, or Firm*—Sherman & Shalloway

[57] ABSTRACT

In a process for producing an acrylic or methacrylic ester by esterifying acrylic or methacrylic acid with a lower aliphatic alcohol having 1 to 3 carbon atoms in the presence of an acidic catalyst, the improvement which comprises (1) distilling the resulting esterification reaction mixture while feeding the acrylic or methacrylic ester into a distillation column from outside the system, thereby to yield as a distillate a mixture composed of the acrylic or methacrylic ester, water and the unreacted alcohol and being substantially free from acrylic or methacrylic acid, and (2) recycling the residue in the distillation column, from which the ester and water formed have been substantially removed, to the esterification reaction in such a proportion that the mole ratio of acrylic or methacrylic acid to the alcohol in the entire starting materials fed to the esterification reaction is kept at 1:0.5-1.0.

6 Claims, 1 Drawing Figure

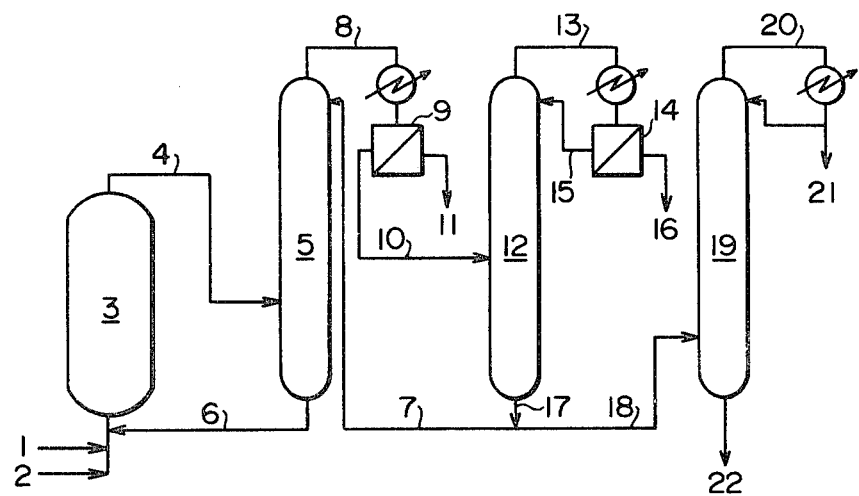

PROCESS FOR PRODUCING ACRYLIC OR METHACRYLIC ESTERS

This invention relates to a process for producing an acrylic or methacrylic ester (to be referred to hereinbelow as a (meth)acrylic ester). More specifically, this invention pertains to an improvement in a process for continuously producing a (meth)acrylic ester by directly esterifying acrylic or methacrylic acid (to be referred to hereinbelow as (meth)acrylic acid) with a lower aliphatic alcohol having 1 to 3 carbon atoms in the presence of an acidic catalyst at low mole alcohol-to-acid ratios.

It is well known that the esterification reaction of (meth)acrylic acid with lower aliphatic alcohols such as methanol, ethanol or isopropanol yields the corresponding esters. It is also known that since this reaction is an equilibrium reaction, the resulting product contains the unreacted alcohol, (meth)acrylic acid and water formed by the reaction in addition to the desired (meth)acrylic ester. A distillating operation has previously been utilized in order to separate the (meth)acrylic ester and water from the reaction product. However, because there is a strong affinity between water and (meth)acrylic acid, (meth)acrylic acid tends to accompany water inevitably when distilling off the water. These substances cannot be satisfactorily separated from each other even if the number of trays or the reflux ratio is increased. This complicates the step of purifying the (meth)acrylic ester and causes various inconveniences such as the occurrence of much waste water. When the mole ratio of the alcohol to (meth)acrylic acid in the starting feed in esterification is decreased, the amount of (meth)acrylic acid which distills off together with water tends to increase. Accordingly, it has been the previous practice to maintain this mole ratio at as high as from 3 to 5 during the esterification reaction, and a great deal of cost must go into the recovery of the unreacted alcohol, the increasing of the capacity of the reactor, the increasing of the utilities, etc.

On the other hand, in order to reduce the strong affinity between water and (meth)acrylic acid, attempts have been made to add an azeotroping agent having higher affinity for water, and distill off the water formed as a result of the reaction from the reaction product as an azeotrope with the azeotroping agent. Benzene, toluene, xylene, etc. are used as such an azeotroping agent. Such a procedure, however, is quite disadvantageous from an economic viewpoint because the operation of separating the (meth)acrylic ester from the azeotroping agent is not easy and complex steps including the recovery of the azeotroping agent are required.

It is an object of this invention to remove the defects of the above-described prior techniques, and provide a process for continuously producing a (meth)acrylic ester directly from (meth)acrylic acid and a lower aliphatic alcohol.

According to this invention, there is provided, in a process for producing an acrylic or methacrylic ester by reacting acrylic or methacrylic acid with a lowr aliphatic alcohol having 1 to 3 carbon atoms in the presence of an acidic catalyst, the improvement which comprises (1) distilling the resulting esterification reaction mixture while feeding the acrylic or methacrylic ester into a distillation column from outside the system, thereby to yield as a distillate a mixture composed of the acrylic or methacrylic ester, water formed as a result of the reaction, and the unreacted alcohol and being substantially free from acrylic or methacrylic acid, and (2) recycling the residue in the distillation column, from which the ester and water formed have been substantially removed, to the esterification reaction in such a proportion that the mole ratio of acrylic or methacrylic acid to the alcohol in the entire starting materials fed to he esterification reaction is kept at 1:0.5–1.0.

Since according to the process of this invention, the mole ratio of the lower aliphatic alcohol to (meth)acrylic acid to be fed to the reaction system is as low as 1:0.5–1.0, the process of alcohol recovery can be greatly simplified, and utilities such as steam can be drastically curtailed. Furthermore, the (meth)acrylic ester can be obtained in a much higher yield than in the conventional processes relative to both (meth)acrylic acid and the alcohol.

Because the esterification between (meth)acrylic acid and the lower aliphatic alcohol is an equilibrium reaction, the reaction product necessarily contains the unreacted alcohol and (meth)acrylic acid. The present inventors have found that in order to obtain the desired (meth)acrylic ester with a good efficiency by distilling the reaction product, it is necessary to feed the same kind of (meth)acrylic ester as the desired product into the distillation column from its top during the distillation, and by so doing, it is possible to obtain as a distillate a mixture composed of the (meth)acrylic ester, water and a small amount of the unreacted alcohol and being substantially free from the unreacted (meth)acrylic acid.

The residue in the distillation column composed of the unreacted (meth)acrylic acid, a small amount of water and a small amount of the (meth)acrylic ester is recycled to the esterification reactor for re-use in the esterification reaction. The amount of the recycle is preferably one or more times the weight of the freshly fed starting materials. If the proportion of (meth)acrylic acid is excessive in the starting mixture fed to the esterification reaction, the formation of impurities (mainly, an alkoxy compound) in the esterification reaction decreases drastically. This means that the yield of the desired product increases both on the basis of (meth)acrylic acid and the alcohol. Investigations of the present inventors show that if the distillation residue is recycled to the esterification reactor in such a proportion that the mole ratio of (meth)acrylic acid to the alcohol in the starting materials fed to the esterification reactor is kept at 1:0.5–1.0, the yield of the (meth)acrylic ester can be increased to 96 to 99% based on (meth)acrylic acid and 97 to 99.5% based on the alcohol while in the prior art it is 91 to 94% based on the former and 94 to 97% based on the latter.

In addition to controlling the recycling of the distillation residue to the reactor as above, the distillation of the reaction product is also controlled such that the desired (meth)acrylic ester is withdrawn as a distillate in an amount in which it must be formed if substantially 100% of the fed (meth)acrylic acid is converted to the ester. By so doing, the continuous manufacturing process for (meth)acrylic esters can be carried out smoothly.

The distillate containing the (meth)acrylic ester and water, which has come out of the distillation column, is separated into two layers. The water layer is submitted to a recovery step for recovering the alcohol and the (meth)acrylic ester contained in it. From the oil layer, the alcohol and water are separated to obtain the (meth-)acrylic ester. Since the process of this invention is carried out at a low acid-to-alcohol ratio, the amount of the unreacted alcohol is very small, and an extraction step for the recovery of the alcohol required in the prior art is not necessary in this invention. Thus, the process can be greatly simplified.

Preferably, as stated hereinabove, the distillation residue consisting mainly of (meth)acrylic acid is recycled to the esterification reactor so that its amount is 1.0 or more times the weight of the (meth)acrylic acid and the alcohol to be freshly fed to the esterification reactor. Increasing the amount of the recycle does not so much affect the reaction, but too large an amount serves no purpose. Amounts more than 7 times the weight of the starting materials freshly supplied to the reactor are not required. When it is desired to obtain methyl acrylate, the amount of the recycle is preferably 1.0 to 2.0 times, and when methyl methacrylate or ethyl or isopropyl (meth)acrylate is desired, it is preferably 2.0 to 5.0 times. The mole ratio of (meth)acrylic acid to the alcohol in the starting materials to be freshly fed into the esterification reactor is 1:1.0–2.0, preferably 1:1.1–1.5.

The acidic catalyst used in this invention may, for example, be a liquid catalyst such as p-toluenesulfonic acid, sulfuric acid, sulfonic acid or hydrochloric acid or a solid acid catalyst such as a strongly acidic ion-exchange resin. The solid acid catalyst is especially advantageous.

The esterification reaction is usually carried out in the presence of a polymerization inhibitor such as hydroquinone, hydroquinone monomethyl ether and phenothiazine. It is used in an amount of 0.0005 to 0.5% by weight based on the weight of (meth)acrylic acid. Suitably, the esterification reaction is carried out at a temperature of 60° to 100° C., preferably 60° to 90° C. under a pressure sufficient to maintain the reaction system liquid, usually under atmospheric pressure or a slightly elevated pressure (0.5–2.0 kg/cm$^2$·G). The residence time of the starting materials in the reactor is at least 0.5 hour, usually 0.5 to 20 hours, preferably 0.5 to 10 hours. Longer periods of time are not economically advantageous.

One preferred embodiment of the process of this invention is described below with reference to the accompanying drawing which is a process flow sheet suitable for the practice of the process of this invention.

(Meth)acrylic acid and an alcohol are freshly fed through lines 1 and 2, respectively, and a distillation residue in a distillation column 5 containing a large amount of the unreacted (meth)acrylic acid is recycled through a line 6. The freshly supplied (meth)acrylic acid, the freshly supplied alcohol and the residue containing the unreacted (meth)acrylic acid are mixed and sent to a reactor 3 having an acid catalyst therein. Preferably, the distillation residue is partly or wholly subjected to a purifying means such as a thin film evaporator prior to recycling. As a result of the purification, high-boiling compounds, polymerized products, etc. present in it are removed and the accumulation of high-boiling components in the reaction system can be prevented.

In the reactor 3, (meth)acrylic acid and the alcohol are reacted nearly to an equilibrium point. The reaction mixture consisting of the (meth)acrylic ester, water, the unreacted alcohol and (meth)acrylic acid is fed to a distillation column 5 through a line 4. In the distillation column 5, the (meth)acrylic ester in an amount substantially equal to the theoretical amount of the ester from the starting (meth)acrylic acid and alcohol is distilled out together with water and the unreacted alcohol while feeding the same kind of (meth)acrylic ester into the distillation column 5 throught a line 7. (Meth)acrylic acid does not substantially distill. The amount of the (meth)acrylic ester fed through the line 7 should be such that the water content of the distillate is 3 to 8% by weight, preferably 5 to 7% by weight, in the case of methyl acrylate, and 8 to 13.5% by weighht, preferably 11.0 to 13.5% by weight, in the case of methyl methacrylate, and ethyl and isopropyl (meth)acrylates. The (meth)acrylic ester to be fed into the distillation column 5 may also be the ester from a line 10 or 21. Economically, however, the ester from the line 7 is preferred.

The distillate is sent to an oil-water separating tank 9 through a line 8.

The (meth)acrylic ester layer separated in the oil-water separating tank 9 is fed to a low-boiling component separating column 12 through the line 10 optionally via an extracting column. In the low-boiling component separating column 12, the alcohol, water and low-boiling impurities are separated, and the (meth)acrylic ester is taken out from the bottom of the column through a line 17. A part of it is recycled to the distillation column 5 through the line 7, and the remainder is fed to a rectification column 19 through a line 18.

The (meth)acrylic ester, the alcohol and water distilled in the low-boiling component separating column 12 are sent to an oil-water separating tank 1 through a line 13, and the (meth)acrylic ester layer is recycled to the top of the column through a line 15. The water layers separated in the oil-water separating tanks 9 and 14 are taken out through lines 11 and 16, and, as required, sent to an alcohol recovering column. The alcohol and the (meth)acrylic ester are recovered, and again fed to the reactor through the line 2. The (meth)acrylic ester purified in the rectifying column 19 is withdrawn as a product through lines 20 and 21, and meanwhile, the distillation residue is withdrawn from the bottom of the column through a line 22.

The following examples illustrate the process of this invention more specifically. It is to be noted however that the invention is not limited to these examples alone.

EXAMPLE 1

A starting liquor composed of 5.0 kg (69.4 moles) of acrylic acid and 2.91 kg (83.1 moles) of methanol containing 0.2% by weight of water and 8.3% by weight of methyl acrylate (the mixture further containing 0.05% by weight, based on the acrylic acid, of hydroquinone) was fed hourly together with 11.87 kg/hr of the recycled distillation residue into a stainless steel reactor filled with 35 liters of a strongly acidic cation exchange resin. Thus, the total amount of the mixture fed to the reactor was 19.78 kg per hour, and consisted of 9.1% by weight of methyl acrylate, 14.2% by weight of methanol, 52.7% by weight of acrylic acid and 23.9% by weight of water and byproducts. The reactor was put in a hot water tank to maintain the temperature of its inside at 80° C. In the reactor, 99% of acrylic acid in the starting liquor freshly fed was converted to methyl acrylate.

The reaction mixture withdrawn from the reactor was sent to a distillation column, and distilled at atmospheric pressure while feeding methyl acrylate containing 0.02% by weight of hydroquinone from the top of the column at a rate of 9.77 kg/hr. At this time, the temperature of the top of the column was 69° C., and the temperature of the distillation still was 102° C. In this way, there was obtained 17.53 kg/hr of a distillate consisting of 90.5% by weight of methyl acrylate, 2.5% by weight of methanol, 7.0% by weight of water and less than 0.0005% by weight of acrylic acid from the top of the column. In the meantime, the residue in the distillation column was withdrawn at a rate of 12.0 kg/hr. 2.4 kg/hr of the residue was sent to a thin film evaporator and after removing high-boiling components and polymerized products therein, mixed with the remaining 9.62 kg/hr of the residue and recycled to the reactor.

The distillate from the distillation column was sent to an oil-water separating tank and separated into a methyl acrylate layer and a water layer. Methanol and water were separated from the methyl acrylate layer in a low-boiling component separating column, and the residue was sent to a rectifying column to obtain methyl acrylate. On the other hand, the water layer was mixed with the methanol and water separated in the low-boiling component separating column, and sent to an alcohol recovery column where most of water was removed. The residue was recycled to the reactor.

As a result, methyl acrylate was obtained in a yield of 97.8% based on the acrylic acid used, and the utilization efficiency of methanol was 99%.

EXAMPLE 2

In the same way as in Example 1, a starting liquor composed of 5.0 kg (69.4 moles) of acrylic acid and 4.38 kg (83.3 moles) of ethanol containing 7.6% by weight of water and 4.8% by weight of ethyl acrylate (the mixture further containing 0.05% by weight, based on acrylic acid, of hydroquinone) was mixed with 23.45 kg of the recycled distillation residue, and the resulting mixture was fed hourly into a reactor filled with 70 liters of a strongly acidic cation exchange resin and kept at 80° C. The total amount of the mixture fed to the reactor was 32.83 kg/hour, and consisted of 16.7% by weight of ethyl acrylate, 13.0% by weight of ethanol, 42.3% by weight of acrylic acid and 27.9% by weight of water and by-products. In the reactor, 98% of acrylic acid in the freshly fed starting liquor was converted to ethyl acrylate.

The reaction mixture withdrawn from the reactor was sent to a distillation column, and distilled at atmospheric pressure while feeding 2.72 kg/hr of ethyl acrylate containing 0.02% by weight of hydroquinone from the top of the column. At this time, the temperature of the top of the column was 79° C., and the temperature of the distillation still was 110° C. In this way, 11.93 kg/hr of a distillate was obtained from the top of the column. The distillate consisted of 81.6% by weight of ethyl acrylate, 5.4% by weight of ethanol, 13.0% by weight of water, and less than 0.0005% by weight of acrylic acid. In the meantime, the residue in the distillation column was withdrawn at a rate of 23.62 kg/hr. 2.36 kg/hr of the residue was sent to a thin film evaporator, and after removing high boiling components and polymerized products in it, mixed with the remaining 21.26 kg of the residue and recycled to the reactor.

The distillate from the distillation column was sent to an oil-water separating tank and separated into an ethyl acrylate layer and a water layer. The ethyl acrylate layer was sent to a rectifying column after separating ethanol and water in a light low-boiling component separating column. Thus, ethyl acrylate was obtained.

On the other hand, the water layer was mixed with ethanol and water separated in the low-boiling component separating column, and sent to an alcohol recovery column where most of water was removed. The residue was recycled to the reactor.

As a result, ethyl acrylate was obtained in a yield of 97.5% based on acrylic acid used, and the utilization efficiency of ethanol was 98.6%.

EXAMPLE 3

In the same way as in Example 1, a starting liquor composed of 5.0 kg (58.1 moles) of methacrylic acid and 2.27 kg (69.6 moles) of methanol containing 0.4% by weight of water and 1.3% by weight of methyl methacrylate (the mixture further containing 0.05% by weight, based on methacrylic acid, of hydroquinone) was mixed with 36.35 kg of the recycled distillation residue, and the mixture was fed hourly into a reactor filled with 90 liters of a strongly acidic cation exchange resin and kept at 80° C. The total amount of the mixture fed to the reactor was 43.62 kg/hr, and consisted of 43.8% by weight of methyl methacrylate, 6.8% by weight of mthanol, 43.6% by weight of methacrylic acid and 5.7% by weight of water and by-products. In the reactor, 99% of methacrylic acid in the starting liquor freshly fed was converted to methyl methacrylate.

The reaction mixture withdrawn from the reactor was sent to a distillation column, and distilled at atmospheric pressure while feeding 3.57 kg/hr of methyl methacrylate containing 0.02% by weight of hydroquinone from the top of the column. At this time, the temperature of the top of the column was 85° C., and the temperature of the distillation still was 110° C. In this way, there was obtained 10.71 kg/hr of a distillate consisting of 86.8% by weight of methyl methacrylate, 3.5% by weight of methanol, 9.7% by weight of water and less than 0.0005% by weight of methacrylic acid. In the meantime, the residue in the distillation column was withdrawn at a rate of 36.48 kg/hr. 3.65 kg/hr of the residue was sent to a thin film evaporator, and after removing high-boiling components and polymerized products in it, mixed with the remaining 32.83 kg of the residue and recycled to the reactor.

The distillate from the distillation column was sent to an oil-water separating tank and separated into a methyl methacrylate layer and a water layer. The methyl methacrylate layer was sent to a rectifying column after separating methanol and water in a low-boiling separating column, to obtain methyl methacrylate. In the meanwhile, the water layer was mixed with the methanol and water separated in the low-boiling component separating column, and sent to an alcohol recovery column where most of water was removed. The residue was recycled to reactor.

As a result, methyl methacrylate was obtained in a yield of 97.5% based on methacrylic acid used, and the utilization efficiency of methanol was 99.5%.

What we claim is:

1. In a process for producing an acrylic or methacrylic ester by esterifying acrylic or methacrylic acid with a lower aliphatic alcohol having 1 to 3 carbon atoms in the presence of an acidic catalyst, the improvement which comprises
    (1) distilling the resulting esterification reaction mixture in a distillation column to produce a distillate comprising the acrylic or methacrylic ester, unreacted alcohol, water and any low-boiling impurities while recycling the acrylic or methacrylic ester separated from the unreacted alcohol, water and any low-boiling impurities in the distillate into the distillation column, thereby to yield as said distillate a mixture composed of the acrylic or methacrylic ester, water and the unreacted alcohol and being substantially free from acrylic or methacrylic acid, and (2) recycling the residue from the distillation column, consisting essentially of acrylic or methacrylic acid from which the ester and water formed have been substantially removed, to the esterification reaction in such a proportion that the mole ratio of acrylic or methacrylic acid to the alcohol in the entire starting materials fed to the esterification reaction is kept at 1:0.5–1.0.

2. The process according to claim 1 for producing methyl acrylate from acrylic acid and methanol, wherein the resulting esterification reaction mixture is distilled while recycling methyl acrylate separated from the distillate into the distillation column so that the water content of the distillate is kept at 3 to 8% by weight.

3. The process according to claim 1 for producing ethyl acrylate from acrylic acid and ethanol, wherein the resulting esterification reaction mixture is distilled while recycling ethyl acrylate separated from the distillate into the distillation column so that the water content of the distillate is kept at 8 to 13.5% by weight.

4. The process according to claim 1 for producing methyl methacrylate from methacrylic acid and methanol, wherein the resulting esterification reaction mixture is distilled while recycling methyl methacrylate separated from the distillate into the distillation column so that the water content of the distillate is kept at 8 to 13.5% by weight.

5. The process according to claim 1 for producing isopropyl acrylate from acrylic acid and isopropanol, wherein the resulting esterification reaction mixture is distilled while recycling isopropyl acrylate separated from the distillate into the distillation column so that the water content of the distillate is kept at 8 to 13.5% by weight.

6. The process according to claim 1 wherein the mole ratio of acid to alcohol in the feed to the esterification reaction, exclusive of the recycled acid, is from 1:1 to 1:2.

* * * * *